United States Patent
Kasdan

Patent Number: 5,822,447
Date of Patent: Oct. 13, 1998

[54] METHOD OF ANALYZING PARTICLES IN A SAMPLE AND DISPLAYING SAME

[75] Inventor: Harvey Lee Kasdan, Van Nuys, Calif.

[73] Assignee: International Remote Imaging Systems, Inc., Chatsworth, Calif.

[21] Appl. No.: 839,580

[22] Filed: Apr. 15, 1997

Related U.S. Application Data

[63] Continuation of Ser. No. 632,310, Apr. 15, 1996, abandoned, which is a continuation of Ser. No. 363,394, Dec. 23, 1994, abandoned.

[51] Int. Cl.⁶ .................................................. G06K 9/00
[52] U.S. Cl. ........................................ 382/133; 382/224
[58] Field of Search .................................. 382/128, 133, 382/134, 164, 168, 170, 171, 173, 181, 190, 192, 203, 209, 217, 224, 225, 226, 227, 228, 305, 306, 165; 356/335, 39; 364/497, 555, 550; 283/58, 57; 435/370, 379; 434/156; 424/93.1; 340/870.27

[56] References Cited

U.S. PATENT DOCUMENTS

| | | | |
|---|---|---|---|
| 4,125,828 | 11/1978 | Resnick et al. | 382/134 |
| 4,338,024 | 7/1982 | Bolz et al. | 356/23 |
| 4,612,614 | 9/1986 | Deindoerfer et al. | 364/415 |
| 5,123,055 | 6/1992 | Kasdan | 382/6 |
| 5,162,990 | 11/1992 | Odeyale et al. | 364/413.1 |
| 5,216,623 | 6/1993 | Barrett et al. | 364/550 |
| 5,235,522 | 8/1993 | Bacus | 382/133 |
| 5,257,182 | 10/1993 | Luck et al. | 382/133 |
| 5,559,022 | 9/1996 | Naughton et al. | 435/240.2 |

OTHER PUBLICATIONS

Graphic Presentation Simplified, By R.R. Lutz, Funk & Wagnalls Co., NY, 1949, "Table of Contents" (pp. vii–x), Pictorial Charts (pp. 112–115). Bar Graphs & Column Charts (pp. 54–78).

Handbook of Graphic Presentation, By C.F. Schmid, The Ronald Press Co., NY, 1954, "Table of Contents" (pp. v–vii), Chapter 9, Pictorial Charts (pp. 223–244).

*Primary Examiner*—Leo H. Boudreau
*Assistant Examiner*—Bijan Tadayon
*Attorney, Agent, or Firm*—Limbach & Limbach L.L.P.

[57] ABSTRACT

A method and an apparatus for analyzing particles in a fluid sample is accomplished by distributing the sample over an extended area. A plurality of optical still images is taken of the sample, with each image representing a different portion of the area. Each optical image is converted into an electronic image, with the images of the particles in the electronic images. Each electronic image is classified into one of a plurality of classifications of visually discernible characteristics. For each classification, the percentage of the total number of particles classified is determined. The images of the particles are extracted from the electronic images. The images of the particles are displayed in an ordered array by the classification with the number of particles within each classification so displayed being proportional to the percentage determined of the total number of particles displayed.

46 Claims, 3 Drawing Sheets

METHOD OF ANALYZING PARTICLES IN A SAMPLE AND DISPLAYING SAME

This is a continuation of application Pat. No. 08/632,310 filed on Apr. 15, 1996, now abandoned, which is a continuation of 08/363,394 filed on Dec. 23, 1994, now abandoned.

TECHNICAL FIELD

The present invention relates to a method and apparatus of analyzing particles in a fluid sample and more particularly to a method and apparatus of analyzing biological fluid samples, and displaying same in a format which is more conveniently understandable to a user.

BACKGROUND ART

Heretofore, methods and apparatuses for analyzing particles in a fluid sample, electronically, and displaying the resultant electronic images of the particles in an ordered array, is well known. See, for example, U.S. Pat. No. 4,612,614.

SUMMARY OF THE INVENTION

A method of analyzing particles in a fluid sample comprises distributing the sample over an extended area. A plurality of optical still images of the sample over the area are taken, with each optical image representing a different portion of the area. Each of the optical images is converted into an electronic image with the images of the particles in electronic form. Each electronic image of a particle is classified into one of a plurality of classifications of visually discernible characteristics. The number of particles in each classification as a percentage of the total number of particles classified, is determined. The images of the particles in electronic form are extracted from the electronic images and are displayed in an ordered array by the classifications, with the number of particles within each classification so displayed being proportional to the percentage determined of the total number of particles displayed.

An apparatus to accomplish the foregoing method is also disclosed.

DETAILED DESCRIPTION OF THE INVENTION

The method of the present invention comprises distributing over an extended area a fluid sample containing particles, such as blood or urine. The distribution can be done, for example, by smearing the sample over a microscope slide 33, such that the particles of interest substantially do not overlap one another. In a typical microscopic smear, involving a fluid sample such as blood, it is possible to find Red Blood Cells (or RBCs) overlapping one another, but with White Blood Cells (WBCs) sparse in the field of view and not overlapping one another. In that event, if the WBCs are the particles of interest, the method of the present invention can be practiced. So long as the particles of interest substantially do not overlap one another, the method of the present invention can be practiced. A plurality of optical still images of the sample are taken, with each image representing a different portion of the slide 33. Thus, for example, the slide 33 with the sample thereon may be mounted in a microscope such that a portion of the slide 33 is in the imaging area as the slide 33 is moved about. Each image will be of a different portion of the slide 33.

Figure 2:
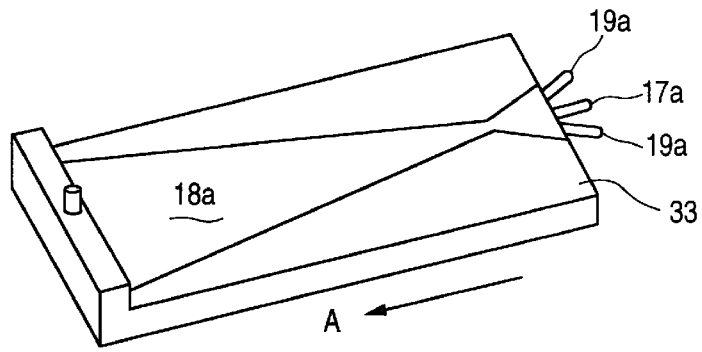
FIG. 2 is a perspective view of a prior art flow chamber suitable for use with the apparatus of FIG. 1 for the method of this invention.
Figure 3:
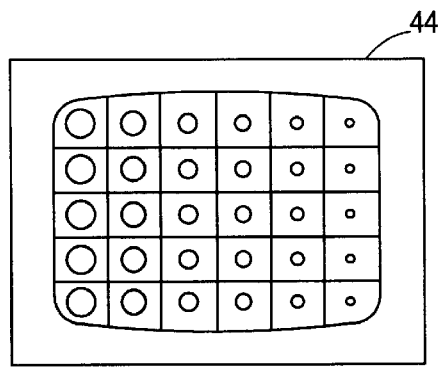
FIG. 3 is a sample of a prior art display showing images of particles arranged in an ordered array by classes of visually discernible characteristics.

The method of the present invention can also be practiced by the use of a flow cell 33, shown in FIG. 2. The flow cell 33 is of the type fully described in U.S. Pat. No. 4,338,024. A sample fluid, such as blood or urine, is sent into the flow cell 33 through first input 17a. Sheath fluids are provided to the flow cell 33 through the second inputs 19a. The sample fluid is moved through the flow cell 33 in the direction shown by arrow A. The sample fluid is distributed over an extended area 18a, which has a width many times the thickness, with each measured perpendicular to the direction of flow. The sample fluid is distributed such that the particles of interest substantially do not overlap one another in the extended area 18a. The sample fluid in the flow cell 33 is placed under the microscope 32 with the microscope 32 focused on the extended area 18a. As the sample fluid moves through the flow cell 33, the microscope 32 takes an optical image of the fluid in the viewing area 18a. Since the fluid is moving, the apparatus 30 is held stationery. Thus, the images formed at the microscope 32 are of different portions of the sample fluid.

Finally, the method of the present invention can also be practiced by imaging biological particles or cells in vivo, as for example, disclosed in U.S. Pat. No. 4,998,553. In that event, the sample need not be "distributed" over an extended area as for a microscopic slide or for a flow cell.

Each of the optical images obtained from a slide or from a flow cell 33, shown in FIG. 2, is converted into an electronic image. The images of the particles are in the electronic images. Each electronic image of the particles is classified into one of a plurality of classifications of visually discernible characteristics. The number of particles in each classification and the corresponding percentage of the total number of particles of interest classified, is then determined. The images of the particles in electronic form are extracted from the electronic images. The images of a plurality of particles are then composited into a single resultant electronic image, with the plurality of particles displayed in an ordered array by classifications. The number of particles within each classification so displayed is proportional to the percentage determined. In addition, the area occupied by the images of particles of each classification is proportional to the percentage determined of that classification to the total area of the display.

Figure 1:
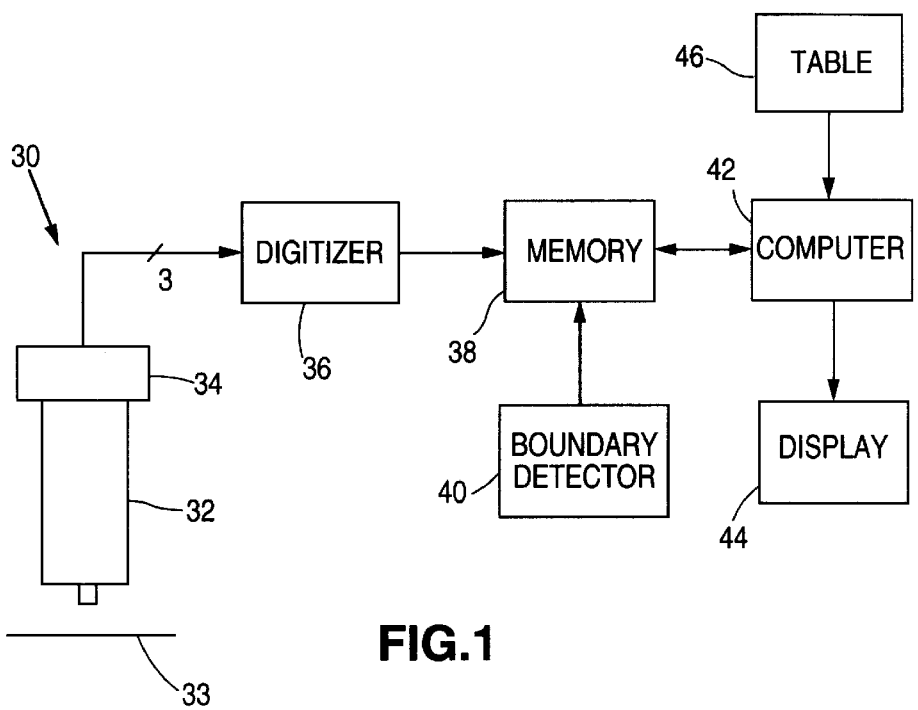
FIG. 1 is a perspective view of an apparatus of the present invention which can be used to carry out the method of this invention.

The method of the present invention can be practiced by using an apparatus 30, shown in FIG. 1. The apparatus 30 comprises a microscope 32, which is focused on an examination area 33. As previously discussed, the examination area can be a microscopic slide 33 or a flow cell 33 such as that disclosed in U.S. Pat. No. 4,338,024. A camera 34 is attached to the microscope 32 and is adapted to image a portion of a suspension having a particle therein. The camera 34 is preferably of a raster scan type and may be a CCD camera model XC711 manufactured by Sony. The camera 34 can form an electrical image of the field of view as seen through the microscope 32. Further, the camera 34 segments the image into a plurality of pixels, with an electrical signal corresponding to each pixel of the image. The camera 34 also outputs a plurality of signals (3) one for each of the colors (Red, Blue, and Green).

Each of the signals from the camera 34 is supplied to a digitizer 36, which digitizes the image intensity of each pixel into an electrical signal representing the grey scale value. Preferably, the pixel is digitized into a gray scale value between 0 and 255, inclusive.

From the digitizer 36, the digitized gray scale value is supplied to a memory 38, where the values are stored. The memory 38 can be a RAM. A boundary detector 40, such as that disclosed in U.S. Pat. No. 4,538,299 operates on the image in the memory 38 and detects the boundary of the image detected. The result can be stored in the memory 38, or in a separate memory. Such an apparatus 30 is disclosed in U.S. Pat. No. 5,123,055.

The apparatus 30 further can classify the electronic images of the particles of interest into one of a plurality of classifications. For blood fluid sample, these classifications can be, e.g. lymphocyte (LYMP) cells, monocyte (MONO) cells, neutrophil (NE) cells, eosinophil (EO) cells, polymorphonuclear neutrophil (PMN) cells, and basophil (BASO) cells. These classifications of particles can be distinguished from one another by visually discernible characteristics. As disclosed in U.S. Pat.No. 5,123,055, the apparatus 30 can classify the electronic images of the particles into one of a plurality of classifications of visually discernible characteristics.

After the electronic images of the particles have been so classified, the number of particles in each classification as a percentage of the total number of particles classified, is then determined. The images of the particles in electronic form are extracted from the electronic images. The images of a plurality of particles are then composited into a single electronic image, with the plurality of particles displayed in an ordered array by classifications. The total number of particles displayed is proportional to the total number of particles classified, with the number of particles within each classification so displayed being proportional to the percentage determined of the total number of particles displayed. In addition, the area occupied by the images of particles of each classification is proportional to the percentage determined of that classification to the total area of the display.

Figure 4:
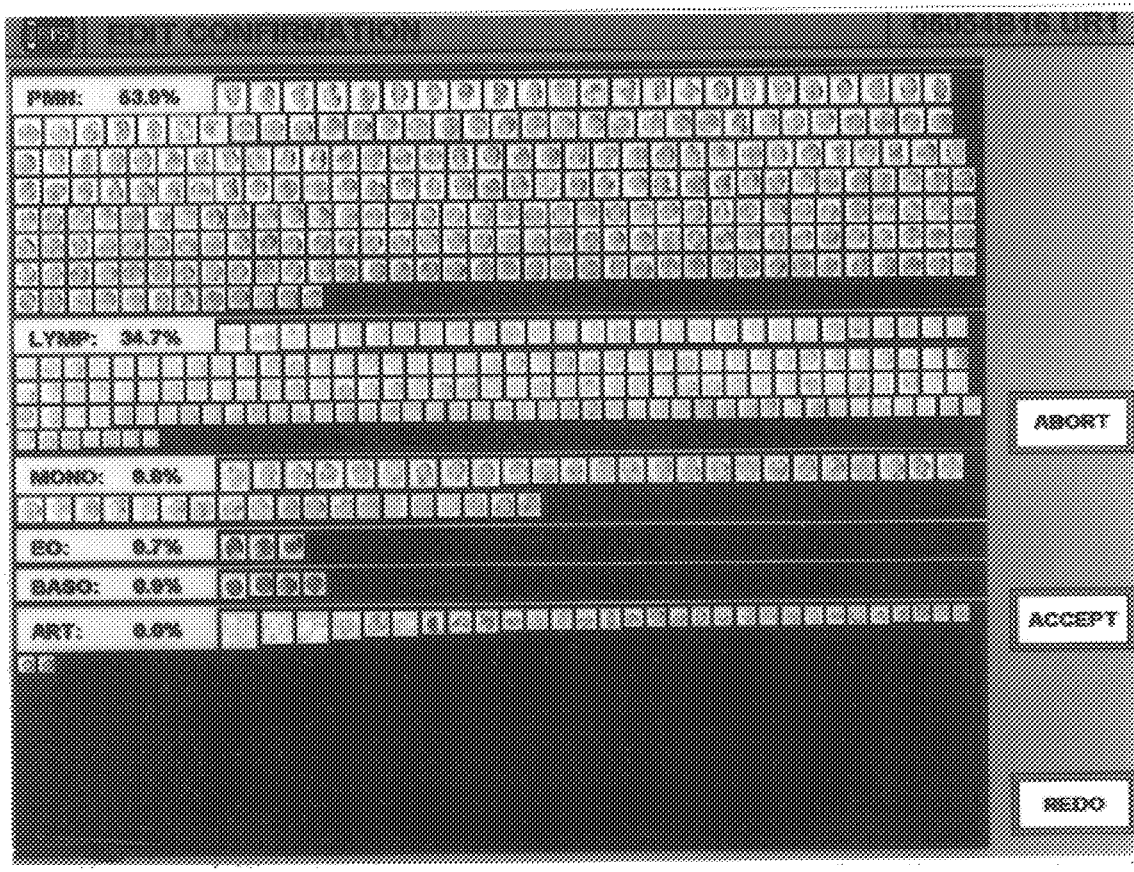
FIG. 4 is a sample of one embodiment of a display in accordance with the method of the present invention.

Referring to FIG. 4, there is shown an example of a display 44 showing the method of the present invention. As can be seen, particles PMN (POLYMORPHONUCLEAR NEUTROPHIL), LYMP (LYMPHOCYTE), MONO (MONOCYTE), EO (EOSINOPHIL), BASO (BASOPHIL), and ART (ARTIFACTS) are displayed. As shown in FIG. 4, 242 images of PMN cells, 156 of LYMP cells, 44 of MONO cells, 3 EO cells, and 4 BASO cells are displayed, for a total of 449 classified cells. Artifacts, are cells which are not classifiable. Hence they are excluded from the total number of particles classified. Therefore, for example, the percentage of PMN particles displayed is as shown equal to (242/449) or 53.9%. Thus, by the method of the present invention, not only are the particles displayed in an ordered array based upon their classification, but the number of particles so displayed is proportional to the numbers actually found in the fluid sample. If the total number of particles or cells classified exceeds the ability of the display 44 to display all of them in a single image, then the method of the present invention displays a total number of particles which is proportional to the total number of particles classified.

Further, for each classification of particles displayed, the number of particles in each classification displayed is proportional to the percentage determined for that classification of the total number of particles displayed. Thus to a user of the apparatus 30, viewing the display 44, the user gains an immediate appreciation of the particles that have been so classified not only by an ordered array but also by the qualitative magnitude differential between the various classifications, even without the actual numeric classifications calculated as shown. A user looking at the screen shown in FIG. 4 would have an immediate appreciation that the number of particles in the fluid sample for PMN type particles is nearly twice as much as the number of LYMP particles in the same fluid sample. The amount of screen display area used to display each classification of particles of interest is proportional to the percentage of the number of particles of interest in a classification that bears to the total number of particles classified. This appreciation of the qualitative magnitude of the particles displayed along with the actual particles themselves classified in the particular classifications is what makes the display 44 unique and the method of the present invention so useful to users of the system 30. The user can almost instinctively and immediately determine, by looking at the display 44, whether the specimen, as represented by the fluid sample, is "normal" or "abnormal", by seeing the amount of screen area used to display a particular classification of particles of interest.

Figure 5:
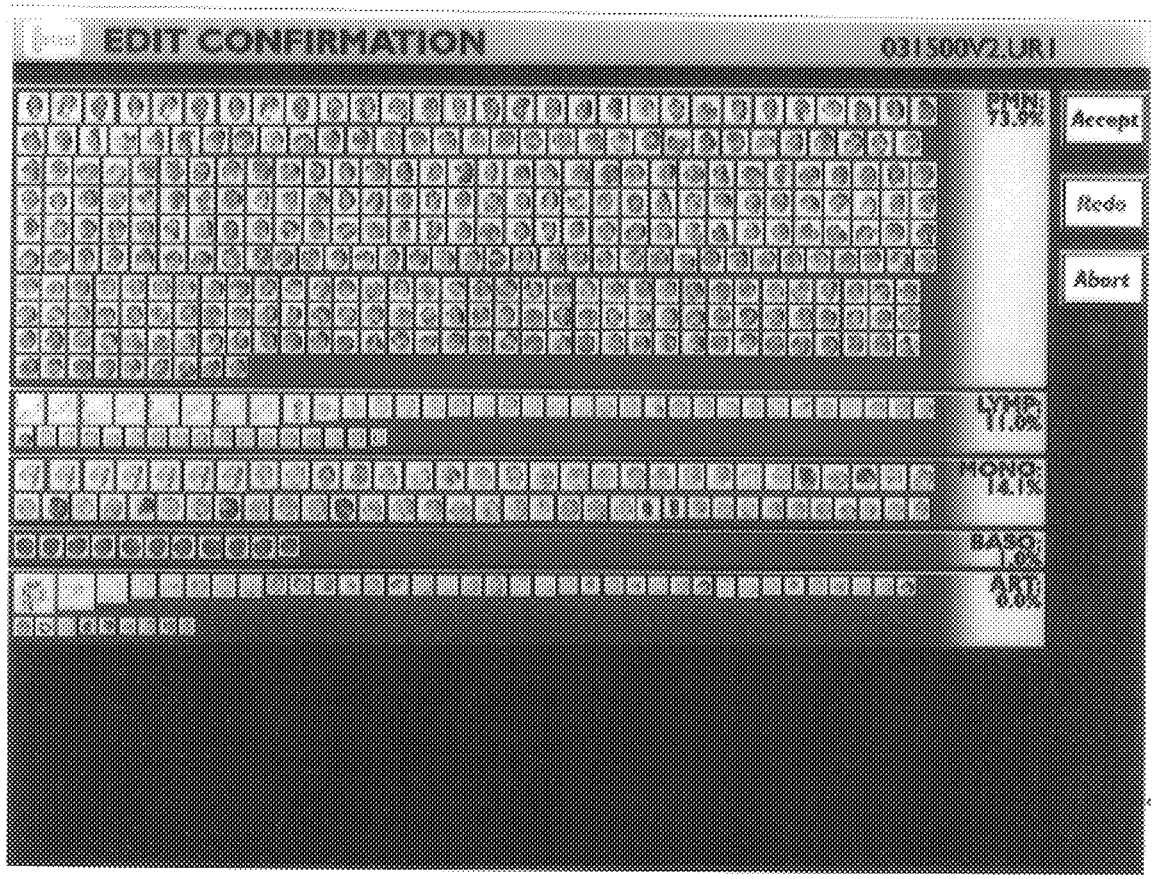
FIG. 5 is a sample of another embodiment of a display in accordance with the method of the present invention.

Referring to FIG. 5, there is shown another embodiment of a display 44, displaying particles classified in accordance with the method of the present invention. In the display 44, as shown in FIG. 5, the particles of interest classified are shown being displayed in an ordered array, with the number of particles in each classification displayed, proportional to the percentage of particles classified, multiplied by the total number of particles displayed. This is just like the display shown in FIG. 4. However, in addition, the display shown in FIG. 5, shows a graphical indicia, namely a bar graph, associated with each classification, shown on the right portion of the display. The length of the bar associated with each classification is proportional to the percentage of particles in that classification that bears to the total number of particles classifiable. This further imparts to the user qualitative information, such as whether the specimen is "normal" or "abnormal."

A wide variety of programming may be employed for further processing each electronic image or the one resultant electronic image with the apparatus of FIG. 1 depending upon the particular task which user wishes to perform.

For example with urine, in the method of the prior art, if chemical particles, such as amorphous phosphates are in the imaging area and obscure the view of the biological particles, the phosphate particles are removed chemically through the addition of hydrochloric acid. With the method of the present invention, however, the chemical particles may be removed electronically, i.e. through image processing techniques. If it is desired to remove particles of particular size, color or shape from view, this may be done electronically without preparing the sample each time. Moreover, with the method of the present invention, biological particles, such as artifacts, which heretofore may not be removed chemically, may be similarly electronically removed from the image. Thus a greater degree of flexibility is possible with the present invention.

In addition, the background image can be subtracted from each electronic image before the images of the particles are composited. Alternatively, the resultant image is formed and then the background image is subtracted from each image of the particles that forms the resultant image.

The images of the particles are displayed on display 44 in an ordered array. By an ordered array, it is meant that images of particles are displayed by classes, each class having a visual characteristic different from the other class. For example, the images can be displayed by size, i.e., the images of the same size particles (presumably representing the same type of particle) are displayed in the same row or same column. An adjacent row or column on display 44, being a different class, will be displayed images of particles having a different size. The visual presentation of images of particles in an ordered array facilitates identification of the type of particle by the user. Apart from size, the display of the images of the particles can be by color, shape or texture (i.e. internal detail of the particle), or any other visually distinguishable characteristic.

The resultant image can also comprise a plurality of images of particles, that are only a certain class or classes of images of particles. For example, a resultant image can be formed with a plurality of images of particles which are characterized by being limited within a range of the size of the particles. Alternatively, the resultant image can be formed with a plurality of images of particles, with an a priori determined class of particles, the images of which are not composited to form the resultant image. In other words, for example, a resultant image can be composited from a plurality of images of particles in an ordered array, such that an a priori determined class of particles, such as a particular size of particles, are not used to form the resultant image.

The images of the particles can be matted for further ease of viewing and identification.

Furthermore, because the display 44 is connected to the processor 42, which retains a count of the number of particles in each class, any editing of the images on the screen of display 44 can also edit the number of particles in each class, stored in memory 38. For example, a sample of urine is examined under the microscope 32. A plurality of optical images are formed with each optical image converted into an electronic image. The portion of each electronic image containing the image of a particle is extracted and is stored in memory 38 (which can include peripheral memory such as a disc drive). The processor 42 determines there are 320 particles of Size A, among others. Because the display 44 has a limited viewing area, the processor 42 displays only sixteen (16) images of particles of Size A. It is assumed that the sixteen images are statistically representative of the 320 images of the particles of Size A. Upon presentation of the sixteen images on display 44, the user can edit the images of the particles of Size A. If, for example, two (2) images of particles of Size A are removed, as discussed above, the processor 42 applies this factor and multiplies the total count accordingly. Therefore, the new count of the number of particles of Size A would be (14/16×320=)280. Thus, with the method of the present invention, manual editing of the images of particles that are presented for viewing is achieved with machine editing of the total count of the number of particles based upon the manual edit. After the display 44 has been edited, the computer 42 would automatically recalculate the percentage of particles of interest for each classification and display the proportional number on the display 44, as well as the proportional graphical indicia.

It should be appreciated that there are many advantages to the method of the present invention. The first and foremost is that the analysis of particles of a fluid sample may be made and with the image in electronic form, a number of imaging techniques may be used to further process the image, including the electronic removal or accumulation of specific chemical and biological particles.

What is claimed is:

1. A method of analyzing a plurality of different particles of interest from a sample comprising:

distributing said sample over an extended area;

forming a plurality of different optical still images of said sample, including said plurality of different particles of interest, over said area, with each different optical still image representing a different portion of said area;

converting each of said different optical still images to a different electronic image thereby converting said different optical still images of said plurality of different particles of interest into different electronic images of said plurality of different particles of interest;

classifying each different electronic image of one of said plurality of different particles of interest into one of a plurality of classifications of visually discernible characteristics;

determining, for each classification, the percentage of the total number of said plurality of different particles of interest classified;

extracting different electronic particle images of said plurality of different particles of interest from said different electronic images; and displaying said different extracted electronic particle images of said particles of interest in a single image in an ordered array by said classifications on a display screen means, with the number of different extracted electronic particle images within each classification so displayed in said single image being proportional to the percentage determined of the total number of said plurality of different particles of interest displayed in said single image, with the total number of said different extracted electronic particle images displayed in said single image being proportional to the total number of said plurality of different particles of interest classified.

2. The method of claim 1, wherein said displaying step further comprising, displaying a graphical indicia of the percentage determined for each classification.

3. The method of claim 2, wherein said graphical indicia is a linear visual indicia.

4. The method of claim 3, wherein said linear visual indicia is a bar graph.

5. The method of claim 2 wherein said graphical indicia is proportional to the area on said display screen means for displaying each classification of different extracted electronic particle images representing said plurality of different particles of interest.

6. The method of claim 1, wherein one of said visually discernible characteristics is size of said particles of interest.

7. The method of claim 1, wherein one of said visually discernible characteristics is color of said particles of interest.

8. The method of claim 1, wherein one of said visually discernible characteristics is shape of said plurality of different particles of interest.

9. The method of claim 1, wherein one of said visually discernible characteristics is texture of said plurality of different particles of interest.

10. The method of claim 1 further comprising the step of editing said display of said images of said plurality of different particles of interest.

11. The method of claim 10 further comprising the step of automatically recalculating the percentage of the total number of plurality of different particles of interest determined for each classification, after said editing step.

12. The method of claim 11 further comprising the step of redisplaying said different extracted electronic images of said plurality of different particles of interest on said screen display means in response to said recalculating step.

13. The method of claim 2 further comprising the step of editing said display of said different extracted electronic particle images of said plurality of different particles of interest.

14. The method of claim 13 further comprising the step of automatically recalculating the percentage of the total number of plurality of different particles of interest determined for each classification, after said editing step.

15. The method of claim 14 further comprising the step of redisplaying said different extracted electronic particle images of said plurality of different particles of interest on said screen display means in response to said recalculating step.

16. The method of claim 14 further comprising the step of: redisplaying said graphical indicia in response to said recalculation step.

17. The method of claim 1 wherein the area of display on said display screen means for each of said classification is proportional to the percentage determined for said classification of the total amount of area of said display screen means.

18. A method of analyzing a plurality of different particles of interest from a moving sample comprising:
 moving said sample in a direction of flow;
 distributing said sample over an extended area having a width and a thickness both measured perpendicular to the direction of flow;
 illuminating said sample at a predetermined location in the direction of flow, with said illumination directed in a direction intersecting the direction of flow;
 forming a plurality of different optical still images of said sample, including said plurality of different particles of interest, at said location;
 converting each of said different optical still images to a different electronic image thereby converting said different optical still images of said plurality of particles of interest into different electronic images of said plurality of different particles of interest;
 classifying each different electronic image of said plurality of different particles of interest into one of a plurality of classifications of visually discernible characteristics;
 determining, for each classification, the percentage of the total number of particles of interest classified;
 extracting different electronic particle images of said plurality of different particles of interest from said different electronic images; and
 displaying said different extracted electronic particle images of said particles of interest in a single image in an ordered array by said classifications on a display screen means, with the number of different extracted electronic particle images within each classification so displayed in said single image being proportional to the percentage determined of the total number of said plurality of different particles of interest displayed in said single image, with the total number of said different extracted electronic particle images displayed being proportional to the total number of said plurality of different particles of interest classified.

19. The method of claim 18, wherein said displaying step further comprising, displaying a graphical indicia of the percentage determined for each classification.

20. The method of claim 19, wherein said graphical indicia is a linear visual indicia.

21. The method of claim 20, wherein said linear visual indicia is a bar graph.

22. The method of claim 19 wherein said graphical indicia is proportional to the area on said display screen means for displaying each classification of different extracted electronic particle images representing said plurality of different particles of interest.

23. The method of claim 18, wherein one of said visually discernible characteristics is size of said particles of interest.

24. The method of claim 18, wherein one of said visually discernible characteristics is color of said particles of interest.

25. The method of claim 18, wherein one of said visually discernible characteristics is shape of said plurality of different particles of interest.

26. The method of claim 18, wherein one of said visually discernible characteristics is texture of said plurality of different particles of interest.

27. The method of claim 18 further comprising the step of editing said display of said images of said plurality of different particles of interest.

28. The method of claim 27 further comprising the step of automatically recalculating the percentage of the total number of plurality of different particles of interest determined for each classification, after said editing step.

29. The method of claim 28 further comprising the step of redisplaying said different extracted electronic particle images of said plurality of different particles of interest on said screen display means in response to said recalculating step.

30. The method of claim 19 further comprising the step of editing said display of said different extracted electronic particle images of said particles of interest.

31. The method of claim 30 further comprising the step of automatically recalculating the percentage of the total number of plurality of different particles of interest determined for each classification, after said editing step.

32. The method of claim 31 further comprising the step of redisplaying said different extracted electronic particle images of said plurality of different particles of interest on said screen display means in response to said recalculating step.

33. The method of claim 31 further comprising the step of redisplaying said graphical indicia in response to said recalculation step.

34. The method of claim 18 wherein the area of display on said display screen means for each of said classification is proportional to the percentage determined for said classification of the total amount of area of said display screen means.

35. A method of analyzing a plurality of different particles of interest in a sample comprising:
 imaging said sample over an imaging area, to form a plurality of different optical images, including said plurality of particles of interest;
 converting each of said different optical images to an electronic image thereby converting different optical images of said plurality of particles of interest into different electronic particle images of said plurality of particles of interest;
 classifying said different electronic particle images of said plurality of different particles of interest into one of a plurality of classifications of visually discernible characteristics;

determining, for each classification, the percentage of the total number of plurality of different particles of interest classified; and displaying said different electronic particle images of said particles of interest in a single image in an ordered array by said classifications on a display screen means, with the number of different electronic particle images within each classification so displayed in said single image being proportional to the percentage determined of the total number of different electronic particle images of particles of interest displayed in said single image, with the total number of different electronic particle images representing particles of interest displayed in said single image being proportional to the total number of plurality of different particles of interest classified.

36. The method of claim 35, wherein said displaying step further comprising, displaying a graphical indicia of the percentage determined for each classification.

37. The method of claim 36, wherein said graphical indicia is a linear visual indicia.

38. The method of claim 37, wherein said linear visual indicia is a bar graph.

39. The method of claim 36 wherein said graphical indicia is proportional to the area on said display screen means for displaying each classification of plurality of different particles of interest.

40. The method of claim 35 further comprising the step of editing said display of said images of said plurality of different particles of interest.

41. The method of claim 40 further comprising the step of automatically recalculating the percentage of the total number of plurality of different particles of interest determined for each classification, after said editing step.

42. The method of claim 41 further comprising the step of redisplaying said different electronic particle images of said plurality of different particles of interest on said screen display means in response to said recalculating step.

43. The method of claim 36 further comprising the step of editing said display of said images of said plurality of different particles of interest.

44. The method of claim 43 further comprising the step of automatically recalculating the percentage of the total number of plurality of different particles of interest determined for each classification, after said editing step.

45. The method of claim 35 wherein the area of display on said display screen means for each of said classification is proportional to the percentage determined for said classification of the total amount of area of said display screen means.

46. An apparatus for analyzing and displaying a plurality of different particles of interest in a sample comprising:

means for imaging said sample over an imaging area, to form a plurality of different optical images, including said plurality of different particles of interest;

means for converting each of said different optical images to an electronic image thereby converting different optical images of said plurality of different particles of interest into different electronic images of said plurality of different particles of interest;

processing means including means for classifying each different electronic image of one of said plurality of different particles of interest into one of a plurality of classifications of visually discernible characteristics; means for determining, for each classification, the percentage of the total number of plurality of different particles of interest classified; means for extracting particle images of said plurality of different particles of interest from said different electronic images, forming a plurality of different electronic extracted particle images; and means for displaying said plurality of different electronic extracted particle images of said particles of interest in a single image in an ordered array by said classifications, with the number of different electronic extracted particle images within each classification so displayed in said single image being proportional to the percentage determined of the total number of plurality of different particles of interest displayed in said single image, with the total number of plurality of different particles of interest displayed in said single image being proportional to the total number of plurality of different particles of interest classified.

* * * * *